US00PP21392P3

(12) United States Plant Patent
Fleming

(10) Patent No.: US PP21,392 P3
(45) Date of Patent: Oct. 19, 2010

(54) ***HIBISCUS* PLANT NAMED 'DAVE FLEMING'**

(50) Latin Name: *Hibiscus moscheutos*
Varietal Denomination: Dave Fleming

(76) Inventor: David Whitman Fleming, Lincoln, NE (US); Gretchen Angela Zwetzig, legal representative, 267 N. Swarthmore Ave., Lindsay, CA (US) 93247

( * ) Notice: Subject to any disclaimer, the term of this patent is extended or adjusted under 35 U.S.C. 154(b) by 0 days.

(21) Appl. No.: 12/317,183

(22) Filed: Dec. 18, 2008

(65) Prior Publication Data

US 2010/0162450 P1 Jun. 24, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner*—Susan B McCormick Ewoldt

(57) ABSTRACT

A new and distinct cultivar of winter hardy *Hibiscus* plant named "Dave Fleming" is the result of a unique hybridization. This new and distinct cultivar is characterized primarily to its novelty by, its extreme cold hardiness to Zone 4, large, thick-textured and very overlapping, reddish-cerise flowers and its floriferous nature from midsummer until frost.

1 Drawing Sheet

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined, 3-5 lobed "oak to maple-shaped" leaves with a purple color and relatively smooth margins which combined compliments the landscape;

(b) Medium-sized flowers that are outstanding for their bright reddish-pink colored, thick textured petals;

(c) The plant being very floriferous with flowers that stay open for at least one full day;

(d) The plant being medium-sized but vigorous with compact and uniform breaking action which gives it unique landscape utility; and (e) The plant being so hardy that it can consistently withstand winter temperatures of at least −30 degrees Fahrenheit.

SUMMARY OF THE INVENTION

'Dave Fleming' was the result of a 40-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 1996 and was selected by David Fleming and Gretchen Zwetzig on David Fleming's property located in Lincoln, Nebr. Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar at 2½ years of age are shown in the attached drawing. More specifically, the drawing is a semi close-up of the flower and the leaf.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart, while general color recitations are consistent with ordinary American terminology.

'Dave Fleming' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4).

THE PLANT

Parentage:

*Seed Parent.—Hibiscus moscheutos,* unnamed and unpatented Fleming-bred seedling.

*Pollen Parent.—Hibiscus coccineus,* unnamed and unpatented Fleming-bred seedling.

*Comparison between observed plant and parents.*—Parents are similar to Observed Plant, except for having slightly smaller (1") flowers.

*Comparison between observed plant and other known cultivars.*—The Observed Plant is unique, but most similar to Co-pending Patent applications: 12/317167, 12/317181, 12/317182 and the other patented hardy *Hibiscus* from Fleming's Flower Field, in that (a) they are all more compact at 3 feet on average. (b) they are all hardy to −30 Fahrenheit. © they all have refined new leaf shapes. (d) they all have thick, overlapping new flower colors with blooms from top to bottom of the plants.

Origin: A selected seedling from stated cross.

Type of plant: Hardy, herbaceous perennial.

Classification: Variety of hardy *Hibiscus* plant.

Propagation: Relatively easy to propagate through cuttings; holds its distinguishing characteristics through successive cuttings and divisions.

Size: About 2½-3½ feet tall and about 2½ feet wide.

Form: Symmetrical annual growth from perennial roots.

Habit: Upright and uniformly branched.

Growth: Vigorous; medium and compact. Full grown (3ft) in 2 years.

Hardiness: Hardy to at least −30 degrees Fahrenheit.

General health: Plant is very disease resistant against rot, aphids, spider mites, scale, white fly etc.; sturdy through excessive drought, rain or wind.

Propagation: Relatively easy and fast rooting by cuttings in approximately 2 weeks.

Foliage:

1. *Arrangement.*—Alternate.
2. *Shape.*—Juvenile: 3-5 lobed "maple-shaped" leaves. Rounded base shape. Mature: Refined, "maple-shaped" , 3-5 lobed leaf with entire to mildly serrate margins and acute apices; rounded base.
3. *Size.*—Mature leaf (petiole base to apex): Length is about 6 inches or 16 cm, width is about 10 inches or 25.5 cm.
4. *Color.*—Young leaves (upper side): 147-A, (purple cast) A little darker than 92-A. Mature leaves: (upper side): 147-A, (purple cast) A little darker than 92-A. Veins: Between 147-A and 147-B. Venation pattern: Palmate. Color: 147-A and -B.

*Coloration of the lower leaf surface.*—147-B. 5. Surface texture: Upper. Smooth. Lower: Semi-smooth. 6. Petiole length: About 2¾ inches or 6.5 cm. Diameter: 1-2 cm. 7. Petiole color: 147-B.

Stems: The stems are stout at the base becoming more slender toward the apices; coloration is consistent with the petiole. Stem length: 2-3inches. Diameter: 1-2 cm. Internode length: 2" on average. Texture: Semi-smooth. Stem Color: 147-A and 92-A (cast).

The Flower

Blooming period: Profuse from July until frost.

Flower diameter: Medium; about 10-11 inches (24-27 cm).

Borne: Singly in leaf axils, from midpoint of stems upward.

Bloom duration: Individual bloom last at least one full day.

Form: Campanulate; petals are also very overlapping.

Average number of flowers per season: 300.

Bud:

1. *Length.*—About 2¾ inches or (7 cm) on day before opening.
2. *Color.*—Between 60-A and 60-B.
3. *Surface texture.*—Semi-glabrous.
4. *Duration.*—One to two weeks.

Corolla: Having five petals.

1. *Petal character and dimensions.*—Campanulate and very overlapping. (a) Length: About 5 inches or 12.5 cm. (b) Width: About 6½ inches or 16.5 cm.
2. *Coloration.*—Bright reddish-pink. (a) Reddish-pink petals: 58-A and 58-B. Coloration of lower petal surface: A little lighter than 58-A. (b) Venation in petals: 59-A. Venation pattern: Palmate. Color: 59-A. (c) Eye zone: A little lighter than 46-A. Eye Zone size: 2¾ inches or (6 cm).
3. *Texture.*—Smooth.
4. *Substance.*—Thick.
5. *Shape.*—Campanulate and very overlapping.

Reproductive organs:

1. *Staminal column.*—Stamen along basal two-thirds. Stamen length: About 1½ inches or (3.5 cm). Stamen color: 67-A and 69-B. Pollen color: 162-A.
2. *Style.*—Terminates upper one-third of staminal column. Stigmatic lobe color: 60-A.

Calyx: Connate at the base; about 3½ inches or (8.5 cm) in length. Color: Medium Green: 147-B.

Stipules: None.

Epicalyx: Whorl of bracts.

1. *Shape.*—10-12 slender, sword-shaped bractlets.
2. *Length.*—About 1¼ inches or (4.8 cm).
3. Color.—144-A .

Penduncle:

1. *Length.*—About 1½ inches or (5 cm). Diameter: 1-2 cm.
2. *Strength.*—Stiff and sturdy.
3. *Color.*—Light to medium green with slight reddish-purple cast 147-A and 92-A.

Seeds: Size: 1 cm. Color: Grey. Average number: Less than 100.

GENERAL OBSERVATIONS

This plant. As a hybridized hardy *Hibiscus*, is valuable to the landscape market for its improvements in thicker textured and brightly colored flowers and buds, refined "maple-like" foliage with a purple color, its all-around vigor, good breaking action, and adaptation to extreme environments, including the ability to consistently survive winter temperatures of at least −30 degrees Fahrenheit.

The claim:

1. A new and distinct cultivar of hardy *Hibiscus* plant, as herein shown and described, characterized by its compact nature, refined purplish "maple-shaped" foliage of a purple coloration, its large bright reddish-pink flowers, its vigor and its hardiness.

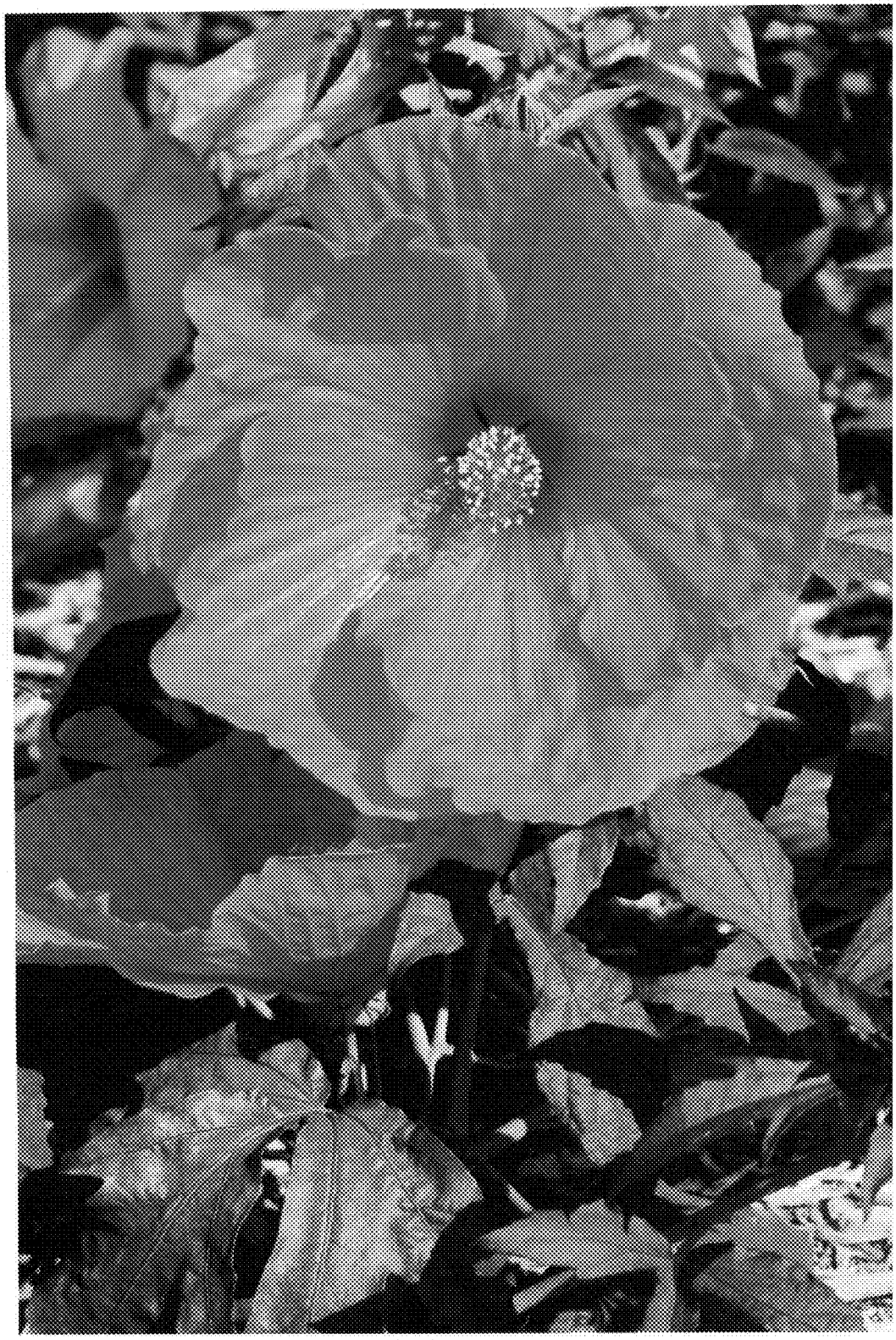

* * * * *